United States Patent [19]

Gunnink et al.

[11] Patent Number: 4,926,113
[45] Date of Patent: May 15, 1990

[54] MEANS AND METHOD FOR CONDUCTOMETRIC PHASE TRANSITION POROSIMETRY

[75] Inventors: Brett W. Gunnink, Columbia, Mo.; Bekir V. Enüstün, Ames, Iowa

[73] Assignee: Iowa State University Research Foundation, Inc., Ames, Iowa

[21] Appl. No.: 301,486

[22] Filed: Jan. 26, 1989

[51] Int. Cl.$^5$ ............................................ G01R 27/02
[52] U.S. Cl. ................................................... 324/694
[58] Field of Search .................. 73/866, 865.8, 73, 74; 324/71.1, 441, 65 R, 65 P, 376; 374/54

[56] References Cited

U.S. PATENT DOCUMENTS

| | | |
|---|---|---|
| 2,526,636 | 10/1950 | Colman . |
| 2,745,057 | 5/1956 | Dotson . |
| 2,802,173 | 8/1957 | Nisle . |
| 3,524,341 | 8/1970 | Roy . |
| 3,965,414 | 6/1976 | Teass, Jr. .......................... 324/441 |
| 4,453,398 | 6/1984 | Demirel et al. . |

FOREIGN PATENT DOCUMENTS 1133506 1/1985 U.S.S.R. .
1198414 12/1985 U.S.S.R. .

Primary Examiner—Robert R. Raevis
Attorney, Agent, or Firm—Zarley McKee, Thomte, Voorhees & Sease

[57] ABSTRACT

A means and method for determination of the pore structure of porous materials using electrical conductance. A sample of porous material is saturated with electrolytic solution and positioned into a container. Temperature and conductance of the sample are monitored as temperature is varied. The temperature is varied so as to create phase transitions in at least a portion of the electrolytic solution existing in the sample. The control means can be utilized to control the sequence of temperature changes and to receive and record the temperature and conductance readings. Alternative means for accomplishing the method of the invention are disclosed, including a specific means for positioning a sample, attaching electrodes to its opposite sides, and attaching a temperature sensing device to the sample, and at the same time isolating and insulating all electrical connections.

10 Claims, 3 Drawing Sheets

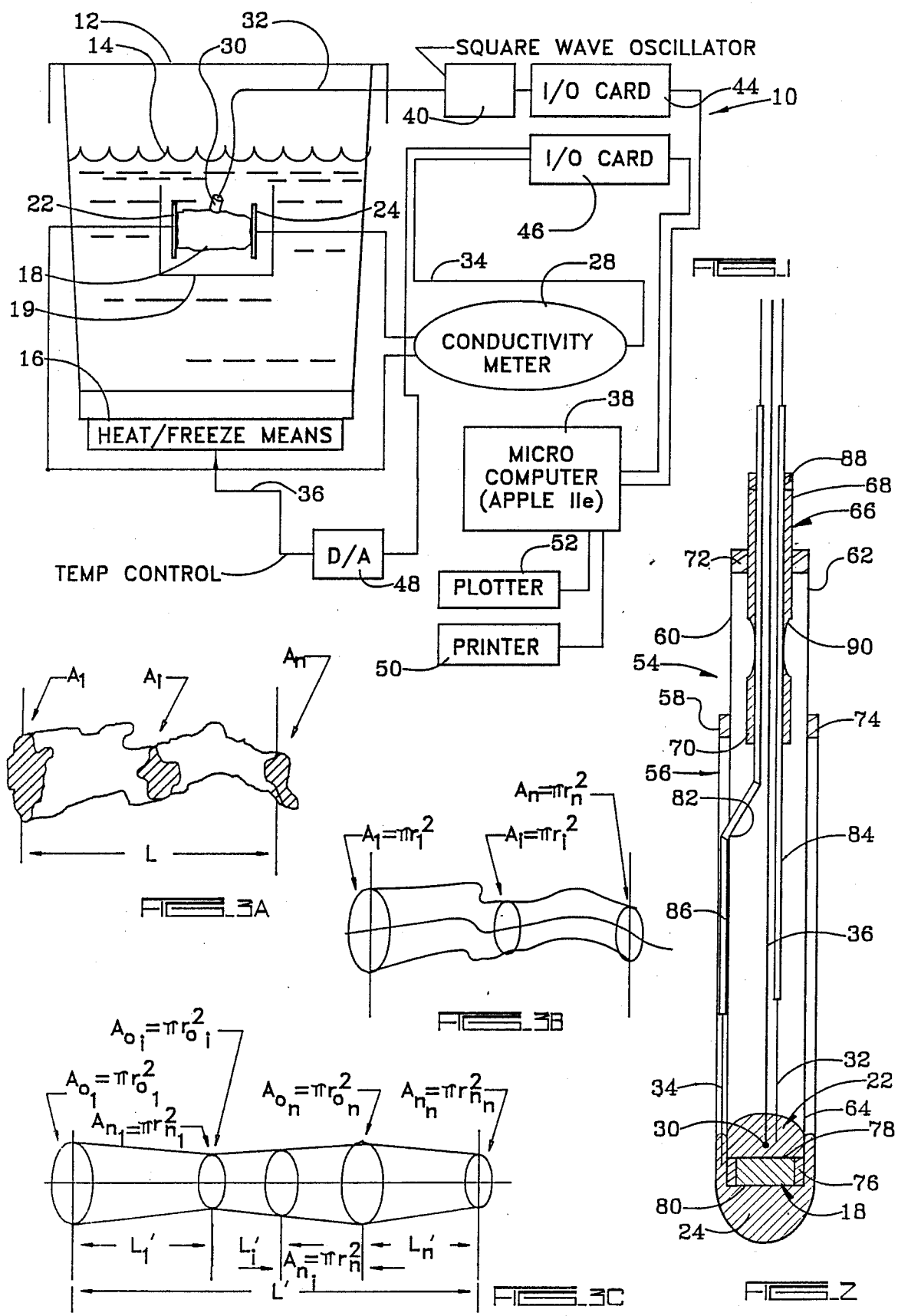

Porous Vycor Glass
-----Cooling Cycle
——Warming Cycle $X = (-1/T)$   $Y = \log C$ $$z\left(-1/T_1, -1/T_0\right) = \int_{(-1/T)}^{(-1/T_0)} \frac{d(\log C)}{d(-1/T)} d(-1/T) - \int_{(-1/T)}^{(-1/T_0)} m\, d(-1/T)$$

Porous Vycor Glass
Warming Cycle

MEANS AND METHOD FOR CONDUCTOMETRIC PHASE TRANSITION POROSIMETRY

BACKGROUND OF THE INVENTION a. Field of the Invention

The present invention relates to a means and method for analysis of porous materials, particularly, to a means and method for determining the volume and size characteristics of the pores of porous materials.

b. Problems in the Art

Various methods have been developed to attempt to characterize the pore systems of porous materials. For example, it is of interest to determine their size, volume-size distribution, and other characteristics.

Conventional methods include mercury porosimetry where a sample of the porous material is saturated with mercury, and then the mercury is expunged and measured. Significant problems exist with such a method. In particular, reliability is compromised by not being able to satisfactorily determine the mercury/matrix contact angle, which is needed for reliable information. The problem of entrapment of the mercury during the procedure also exists.

Another method is capillary condensation porosimetry. Problems with this method include the requirement of elaborate equipment and procedures, and that it is very time consuming.

Other methods used to derive some characteristics of porous materials include measuring changes in temperature and volume during phase transitions of saturated samples. Still further, some pore characteristics are obtainable by measuring the resistivity of a sample and its saturating electrolyte. However, this latter procedure is not useful for the determination of pore size.

There is therefore a real need in the art for a means and method for determining characteristics of the pore structure of a porous material which is non-complex, reliable, efficient in time, and can be utilized for heterogeneous, water-sensitive materials.

It is therefore a principal object of the present invention to provide a means and method for determination of the pore structure of porous materials which improves over or solves the deficiencies and problems in the art.

A further object of the present invention is to provide a means and method as above described which allows for a reliable and efficient determination of such things as pore structure, pore size distribution, and other characteristics of the porous material.

Another object of the present invention is to provide a means and method as above described which is non-complex, and less time consuming than many conventional methods.

A further object of the present invention is to provide a means and method as above described which is reliable for heterogeneous, water-sensitive porous materials.

These and other objects, features, and advantages of the present invention will become more apparent with references to the accompanying specification and claims.

SUMMARY OF THE INVENTION

The present invention includes a means and method for determining the pore structure of porous materials, along with other characteristics, by conductometric phase transition porosimetry. The invention represents an improvement in the reliability and efficiency of gaining such information, while doing so with non-complex apparatus and procedures, and with significant time savings.

The method of the invention saturates the sample of porous material with an electrolytic solution. The temperature imposed upon the sample is then varied and the temperature and conductance of the saturated sample is measured. By knowing the relationships between conductance and temperature; and conductance and pore structure, and freezing temperature and pore size, information regarding pore structure can be derived.

The temperature is varied so as to produce phase change in at least some of the electrolytic solution saturated into the sample. For example, temperature and conductance are measured prior to, during, and after phase changes from liquid to ice for the electrolytic solution, and also for the return phase changes from ice to liquid.

The means of the invention includes a container for holding an isolated sample. The container is placed in an apparatus that is used to vary the temperature of the container and enclosed sample. Electrodes, connected to a conductance meter, are then positioned with respect to the sample. The electrical conductance through the sample is monitored. A temperature monitoring device such as a thermistor is also placed in the sample container and used to monitor the sample's temperature.

Additional enhancements are possible with the invention. Control means can be connected to the apparati measuring temperature and conductance, to record and manipulate such information. Also, the control means are used to vary the temperature of the sample.

The invention also includes a specific apparatus for facilitating the measurement of temperature and conductance over temperature ranges. This specific embodiment includes a structure to reliably hold the sample in position, to position electrodes on opposite sides of the sample, to position a temperature sensing device in, on, or near the sample, and means to keep all of the measuring components and electrodes electrically isolated from one another. A double-open ended tube allows insertion of the sample into one open end. One electrode would be positioned against or implanted into the sample in the interior of the tube. The tube would then be inserted into a test tube having a second electrode in its bottom section. The temperature monitoring device, which can be a thermistor, would also be positioned or implanted with respect to the sample inside the tube. Electrical conduits from each of the electrodes and the thermistor would then be channeled up and out of either the tube or the test tube for connection to appropriate apparatus. Both electrodes and the thermistor would be isolated from one another, as would their conducting wires.

BRIEF DESCRIPTION OF THE DRAWINGS

FIG. 1 is a diagrammatic view of a system according to the invention.

FIG. 2 is a cross-sectional front elevational view of an alternative embodiment for the containment apparatus according to the invention.

FIGS. 3B–C are pictorial depictions of modeling of an irregular pore structure by utilizing right angle truncated cones.

DETAILED DESCRIPTION OF THE PREFERRED EMBODIMENT

Figure 4:
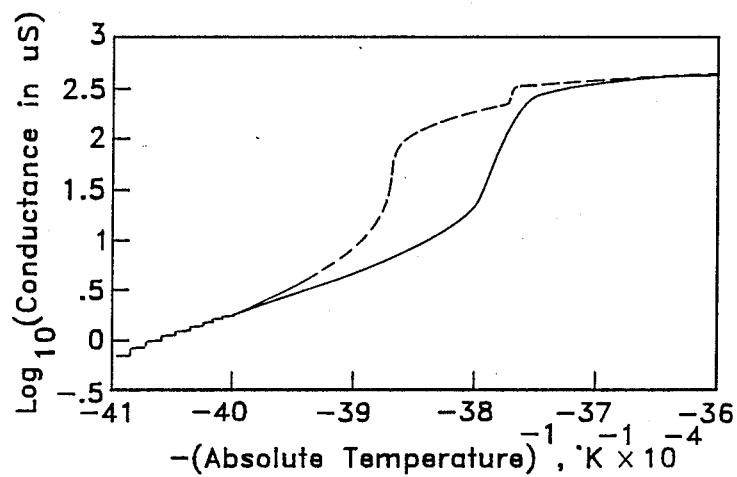
FIG. 4 is a graphic representation of the logarithm of conductance versus negative inverse of absolute temperature (Y versus X) for a material sample analyzed according to the invention.

To aid in the understanding of the invention, specific preferred embodiments of the means and methods for the invention will now be described. Such description includes reference to the drawings, namely FIGS. 1-6. Like parts in the drawings will be referred to by like reference numerals, unless otherwise indicated.

FIG. 1 shows diagramatically one preferred embodiment for a system according to the invention for conductometric phase transition porosimetry. As can be seen, system 10 includes a cyrostat 12 filled with a liquid 14, which in the preferred embodiment is iso-propyl alcohol. Cyrostat 12, as is known in the art, includes a variable temperature component 16 which can vary the temperature inside of cyrostat 12 according to desire. More precisely, it can heat or cool liquid 14 over a range of temperatures. In the preferred embodiment, this range of temperatures includes temperatures both above and below normal freezing, so as to produce phase changes for liquids which freeze at or below the normal freezing point.

A sample 18 of the porous material to be analyzed is saturated with an electrolytic solution and placed in the cyrostat 12 in a suitable container 19. In the preferred embodiment, the electrolytic solution is an ionic solution, and can be a dilute ammonium nitrate solution.

As can further be seen in FIG. 1, the container 19 must hold and position first and second electrodes 22 and 24 in an abutting relationship to opposite sides of sample 18. A conductance meter or monitor 28 continuously monitors electrical conductance between electrodes 22 and 24.

A thermistor 30, such as is known in the art, is also operatively connected with respect to sample 18. Thermistor 30 can either be placed on, into, or near sample 18 to monitor temperature of sample 18.

Thermistor 30 operates as a variable resistor connected to a square wave oscillator 40, which represents the temperature experienced by thermistor 30. Likewise, conductance meter 28 produces a signal which is sent through wire 34 and which represents the level of electrical conductance between electrodes 22 and 24.

The variable temperature component 16 receives signals from computer 38 via I/O card 46 and D/A converter 48 to vary the temperature in cyrostat 12.

It can further be seen that each of wires 32 and 34, are connected at one end to thermistor 30 and conductivity meter 28 respectively, and connected at their other end to the square wave oscillator 40 and I/O card 46. Oscillator 40 is in turn connected to input/output (I/O) cards 44. This allows the signals from thermistor 30 and conductivity meter 28 to be converted to digital format, which in turn can be communicated through the input/output cards to digital computer 38 (which in the preferred embodiment is an Apple IIe micro computer).

This type of interfacing is well known by those skilled in the art. Similarly, signals from computer 38 are sent to digital/analog (D/A) convertor 48 which passes them on to variable temperature component 16 which needs analog signals to operate.

FIG. 1 also shows that printer 50 and/or plotter 52 can be connected to computer 38 to make hard copies of any data stored or recorded in computer 38 such as known in the art.

It can therefore be seen that the system of FIG. 1 allows measurement of temperature and conductance. The system also controls variation of temperature in the interior of cyrostat 12, including variations to cause at least a portion of the electrolytic solution saturated into sample 18 to change physical state.

FIG. 2 depicts another aspect of the invention, namely an optional preferred embodiment for a containment apparatus to hold a sample of porous material, and to provide for accurate and reliable connection for electrodes and channeling of the respective electrical wires from the electrodes and thermistor so that they can be attached to appropriate components. The containment apparatus 54 of FIG. 2 is especially adaptable for sample materials which do not lend themselves easily to direct attaching, implanting or insertion of a thermistor or electrodes.

As can be seen from FIG. 2, containment apparatus 54 utilizes a test tube 56 having a top open 58, an intermediate tube 60 having top and bottom open ends 62 and 64, and a small tube 66 having top and bottom open ends 68 and 70. As can be seen, the size of test tube 56, intermediate tube 60, and small tube 66 are such that they can be succeedingly telescopically fit within one another. They can be secured in the telescopic relationship shown in FIG. 2 by insulating gaskets 72 and 74 which frictionally fit into top open end 62 of intermediate tube 60, and open end 58 of test tube 56 respectively. Gasket 72 and 74 can be made of elastic material, or otherwise, to frictionally fit within those ends and to frictionally receive and secure the respective tube 60 and 66 in the positions shown in FIG. 2.

In FIG. 2, sample 18 is sized so that it can be press-fit into bottom open end 64 of intermediate tube 60, and frictionally secured there by insulating gasket 76, which is similar to gasket 72 and 74. Thus topside 78 of sample 18 is exposed to the interior of intermediate tube 60, whereas the bottom side 80 of sample 18 is exposed to the exterior of intermediate tube 60 and the interior of the lower part of test tube 56.

A first electrode 22 comprising a quantity of mercury is placed in the interior of intermediate tube 60 so that it abutts topside 78 of sample 18. Thermistor 30 is then inserted into first electrode 22 so as to be adjacent topside 78 of sample 18. Conducting wire 32 is also inserted into first electrode 22.

On the other hand, second electrode 24 also consists of a quantity of mercury which is positioned in the bottom of test tube 56. Conducting wire 34 extends down into electrode 24 along the side of intermediate tube 60.

It can therefore be seen that electrodes 22 and 24 abutt opposite sides 78 and 80 of sample 18 and are completely insulated from one another by intermediate tube 60 and insulating gasket 76; so that the only electrically conducting path between electrodes 22 and 24 is through sample 18.

It can further be seen that this arrangement allows for easy positioning of sample 18, easy and flexible abutment of electrodes 22 and 24 to opposite sides of sample 18, and easy insertion of thermistor 30 and conducting wires 32 and 34 in their respective positions. This is accomplished by the liquid state of mercury.

Conducting wire 34 from second electrode 24 extends through a small aperture 82 in the side of intermediate tube 60, and combines with conducting wire 32 and conducting wire 36 connected to thermistor 30 to extend through small tube 66 to the exterior of containment apparatus 54. It can be seen that both conducting wires 32 and 34 have insulation 84 and 86 covering them from a position above the electrodes all the way to the exterior of tube 66 and apparatus 54. Conducting wire 36 is positioned in between wires 32 and 34 even through the interior of small tube 66. An insulating gasket 88 is frictionally fit into the top open end 68 of small tube 66 and serves to compressively and frictionally hold wires 32, 34, and 36 in place. Additionally, small tube 66 could have a constriction 90 in its middle portion to compressively hold the wires in place. Thus, the external ends of wires 32, 34, and 36 are available for connection to components such as A/D converters or D/A converters, such as depicted in FIG. 1.

As previously mentioned, the containment apparatus 54 shown in FIG. 2 is especially used for samples which do not lend themselves to easy embedding of electrodes into the sample, or easy operative connection of a thermistor. An example of such a material is glass, which is porous, but rigid and brittle and presents the problem of electrode and thermistor connection.

The insulating gaskets of the embodiment of FIG. 2 can be tygon tubing. It is to be understood that the upper end of small tube 66 could be filled with a dessicant and cotton to prohibit condensation inside any of the tubes. Tungsten wires were used for wires 32 and 34. Once assembled, the embodiment of FIG. 2 would then be placed inside a cyrostat and the temperature varied. As an example, the iso-propyl alcohol liquid 14 in cyrostat 12 would be lowered from 7° C. to −30° C. at the rate of 3° C. per hour. Conductance and temperature measurements can be taken at 0.1° C. intervals. This would comprise the "cooling" portion of the analytical procedure.

Liquid 14 would then be raised from −30° C. to 7° C. at the same rate and at the same data gathering intervals to comprise the "warming" portion of the test.

It is to be understood that optionally, a resistor could be connected in series with sample 18 in the embodiment of FIG. 2 to provide a more sensitive conductance range available on the conductance meter such as meter 28 showing FIG. 1. For example, in the embodiment of FIG. 2, a five kilo-ohm resistor would allow 0.01 microsiemens ($\mu$S) resolution on meter 28. The gathered values of conductance are then converted to quantitative conductance values using known relationships for conductors connected in series.

The general operation of the invention, and the theoretical basis for the same will now be discussed. It is believed beneficial to briefly describe the theoretical background for deriving results according to the invention, for a complete understanding of the invention.

The present invention utilizes certain premises and assumptions with regard to its methodology. First of all, one needs to understand that pore geometry of any of the samples being evaluated is assumed to be randomly intersecting pores or cylindrical capillaries with or without constrictions. An example of one such pore is shown in FIG. 3a.

Secondly, it is known that the solid-liquid phase transition of water in any pore having an effective radius of r takes place at a temperature, t (°C.) given by:

$$t = -2\gamma T_o/(\rho \lambda r) \quad (1)$$

where $T_o$ is the normal melting point of ice in °K., $\lambda$ is the heat of fusion of ice per unit mass, $\rho$ is the density of water and $\gamma$ is the ice/water interfacial tension at temperature t. In melting, r is the effective pore body radius, while in freezing it is the radius of the pore constriction.

Because many porous materials consist of a non-conducting solid phase and a void system of randomly intersecting capillaries of various sizes, it was determined that by saturating the porous material with an electrolytic solution, it will generally exhibit electrolytic conductance which results from the mobility of ions in the solution.

The parameter called resistivity factor, helpful in this analysis, has been defined as the ratio of resistivity, $\rho_p$ of a porous material completely saturated with an electrolyte, to the resistivity, $\rho_e$ of the electrolyte itself. The resistivity factor, F, has been related to pore structure as follows:

$$F = \rho_p/\rho_e = \tau/\psi \quad (2)$$

where $\tau$ is the tortuosity, defined as the ratio L'/L, where L' is the mean tortous length, of the pore channels in a brine-saturated rock sample traversed by an electrical current flowing between the two ends of the sample separated by distance, L, and $\psi$ is the ratio of the apparent cross-sectional area, A', of the conducting electrolyte to the total cross-sectional area, A, of the sample. Additionally, the resistivity factor can be related to tortuosity and porosity, $\eta$ of the sample by:

$$F = \tau^2/\eta \quad (3)$$

It has been found, however, that equation 3 was true only when pores of the sample have uniform cross-sectional areas.

The relationship of conductivity to pore characteristics is based on the following discoveries. For a cylindrical container of volume V having a cross-sectional area A and length L made of an insulating material, but with ends of a conducting material and filled with a solution of conductivity $\kappa$, the conductance C of the container is:

$$C = \kappa(A/L) = \kappa(V/L^2) \quad (4)$$

If the same container is filled with a porous material saturated with the same solution, conductance will be considerably less since the mean length of path traversed by the current is longer and the cross-sectional area which is available to the current area is smaller.

The conductance of a porous material, C', can be defined as:

$$C' = \kappa V_p/(L^2\omega) \quad (5)$$

where $\kappa$ and L are as defined in equation 4, $v_p$ is the pore volume and $\omega$ is a dimensionless pore geometry factor. This equation can be expanded for the conductance of a pore system consisting of X number of parallel conducting pores as follows:

$$C' = \kappa \frac{V_p}{L^2\omega} = \sum_{j=1}^{j=X} \kappa \frac{V_{pj}}{L^2\omega_j}, \qquad (6)$$

where $C'$, $\kappa$, $V_p$, $L$, and $\omega$ are defined previously, and $V_{pj}$ and $\omega_j$ are the pore volume and geometry factor for individual conducting pore j. It is to be understood from this relationship that if the pore geometry factor for each parallel conducting pore $\omega_j$ is the same, then the pore geometry factor for the pore system, $\omega$, is equal to $\omega_j$.

By again referring to FIG. 3a, a typical irregular single conducting pore channel of a porous material is depicted. According to the present invention, this pore can be represented by a pore with equivalent circular cross-sectional areas as shown in FIG. 3b. This pore would have the same volume and conductance as the irregular pore of FIG. 3a.

Further, according to the present invention, if this circular pore FIG. 3b is stretched so that the curve connecting the centers of the circular cross-sections is alligned, the pore can be represented by a series of right angle truncated cones as shown in FIG. 3c without a change in volume or conductance. The volume of each such cone $V_i$ can be expressed as:

$$V_i = L_i'(\pi/3)r_{oi}r_{ni}(r_{oi}/r_{ni}) + 1 + (r_{ni}/r_{oi}). \qquad (7)$$

By utilizing equation 4, it can then be seen that from infinitesimally small slices the conductance of each cone $C_i$ can be expressed as:

$$\overline{C_i} = \kappa(\pi r_{oi}r_{ni})/L_i' \qquad (8)$$

where $\kappa$ is the conductivity of the pore solution, $L_i'$ is the length of the right truncated cone, and $r_{oi}$ and $r_{ni}$ are the radii of the ends of the cone.

A combination of equations 5, 7, and 8 shows that if the pore system of a porous material when stretched consists of a single right angle truncated cone, then the dimensionless pore geometry factor, $\omega$, can be expressed as:

$$\omega = (\tfrac{1}{3})(L'/L)^2((r_o/r_n) + 1 + (r_n/r_o)). \qquad (9)$$

Using the same approach the pore geometry factor $\omega$ for a pore system consisting of a singular irregular pore (represented by z right angle truncated cones in a series connection, as shown in FIG. 3c) can be expressed as:

$$\omega = \frac{\sum_{i=1}^{i=z}(L_i'r_{oi}r_{ni}((r_{oi}/r_{ni}) + 1 + (r_{ni}/r_{oi})))}{3L^2}\left(\sum_{i=1}^{i=z}L_i'/(r_{oi}r_{ni})\right). \qquad (10)$$

This relationship for a pore of uniform cross-sectional area can be simplified to:

$$\omega = (L'/L)^2, \qquad (11)$$

where $L'$ is the sum of the lengths of the component cylinders (right angle cones with uniform cross-sectional areas) and $L$ is the distance between the ends of the pores as defined previously. The quantity $(L'/L)$ has been commonly referred to as tortuosity. For a pore consisting of uniformly sized right angle truncated cones ($r_{oi}$ and $r_{ni}$ are constant) equation 10 is simplified to the relationship expressed in equation 9. Further if the truncated cones lie in a straight line perpendicular to the end planes of the conducting material, $L'$ will equal $L$ and the pore geometry factor, $\omega$, will be a function of the ratio of the pore neck radii to the pore body radii only for a parameter which previously has been referred to as necking. This illustrates two fundamental characteristics of a pore system, tortuosity and necking, exist which effect the value of the pore geometry factor, $\omega$. This is important with regard to the present invention, which can be called conductometric phase transition porosimetry.

Therefore, considering any pore system to consist of X number of irregular conducting pore channels connected in parallel, an expression for the pore geometry factor, $\omega$, for any pore system as modeled by an agglomoration of right angle truncated cones is:

$$\omega = \frac{\sum_{j=1}^{j=x}\left(\sum_{i=1}^{i=z}L_i'r_{oi}r_{ni}((r_{oi}/r_{ni}) + 1 + (r_{ni}/r_{oi}))\right)_j}{3L^2}\left(\sum_{j=1}^{j=x}\left(\left(\sum_{i=1}^{i=z}L_i'/(r_{oi}r_{ni})\right)^{-1}\right)_j\right)^{-1}. \qquad (12)$$

Therefore, it can be seen that equation 5, containing the pore geometry factor, $\omega$, does provide a relationship between electrical conductance and pore structure.

Because equation 12 provides a complicated expression for pore geometry factor for any pore system, it can be simplified by the assumption that in many materials parallel conducting pores within the material have equivalent geometry pore factors. The pore geometry factor for the entire sample could be evaluated using the relationship given for a single parallel conducting pore (see equation 9). In other words, the sample would be evaluated on the assumption that all pores in the system have basically the same porosity and necking. This does not imply that all pores in the sample are identical but rather that large pores are essentially magnifications of smaller pores.

Knowing this as background, the present invention provides conductometric phase transition porosimetry by utilizing the following assumption. It is assumed that the electrical conductance through the solid phase of a porous material is negligible when compared to the electrolytic conductance of the pore solution saturated into the sample. Additionally, when the temperature of a mass of a saturated porous material sample is raised from sub-freezing temperatures, the frozen pore solution will melt and an increase in electrical conductance will be observed. It is to be understood that capillaries will begin to melt with smaller sizes melting at lower temperatures in accordance with plastic ice theory as expressed in equation 1.

It is further assumed that the relationship between the electrical conductivity of an electrolyte and the absolute temperature of the electrolyte is an Arhennius type of relationship which can be expressed as:

$$\ln \kappa = \frac{a}{T} + b. \qquad (13)$$

where
κ = electrical conductivity,
T = absolute temperature,
a = physical constant, and
b = physical constant.

By combining equations 5 and 13 the following equation is derived:

$$y = mx + d + \log_{10}(V_p/(L^2\omega)) \quad (14)$$

where
L, $V_p$ and $\omega$ are as defined earlier,
x = −1/(absolute temperature),
y = $\log_{10}$ (conductance),
m = physical constant, and
d = physical constant.

A plot of the $\log_{10}$ of the conductance versus the negative inverse of the absolute temperature (Y versus X) for which no phase change occurs will result in a line with a slope equal to m. Below freezing temperatures, the phase change which occurs in a certain range of pores will effectively decrease the volume of the conducting pores. Thus, $V_p$ at below freezing temperatures can be considered to be the volume of conducting pores, $V_{cp}$.

The first derivative of equation 14 yields:

$$\frac{dy}{dx} = m + \frac{d(\log_{10}(V_p/(L^2\omega)))}{dx} \quad (15)$$

Integrating equation 15 over the definite interval, x to $x_0$, yields the following:

$$\log_{10}\left[\frac{\frac{V_{cp}(x_0)}{L^2\omega x_0}}{\frac{V_{cp}(x)}{L^2\omega x}}\right] = \int_x^{x_0} \frac{dy}{dx} dx - \int_x^{x_0} m\, dx \quad (16)$$

The right half of equation 16 can be calculated numerically from conductance test data by graphical integration (see FIG. 6) and is given the variable name Z. Also, it is to be understood if $x_0$ is the value of x at the pore solution melting point, then $V_{cp}(x_0)$ is simply the total conducting pore volume $V_p$. By rearranging equation 16 and referring to pore volume by radius, the following is obtained:

$$\alpha \frac{V_{cp}(r)}{V_p} = 10^{-Z(x,x_0)}, \quad (17)$$

where $V_{cp}$ (r) is the volume of the pores with radii smaller than or equal to r containing unfrozen pore solution, $V_p$ is the total pore volume and $\alpha$ is the ratio of the pore geometry factor of the total pore system, $\omega$, to the pore geometry factor of the pores smaller than r, $\omega_r$. If it is assumed that the shape factor, $\omega$, is independent of pore size, than $\alpha$ is equal to unity and equation 17 can be reduced to:

$$\frac{V_{cp}(r)}{V_p} = 10^{-Z(x,x_0)}. \quad (18)$$

Assuming $\alpha$ to be equal to unity implies the pore system has a certain degree of homogeneity. Again, this does not imply that all the conducting pores are exactly the same, but rather that the tortuosity and necking inherent to a given pore structure is uniform throughout the pore size distribution.

Thus, by utilizing the preferred embodiments described above, the means and method of the invention are accomplished. It can be seen that the invention has achieved at least all of its stated objectives.

FIG. 4 is the logarithm of the conductance plotted against the negative inverse of the absolute temperature for a sample tested (in this case a Vycor glass sample). The linearity of the curves prior to freezing or after melting of capillary water evidences the relationship between electrical conductivity of an electrolyte and temperature as defined in equation 13. The sharp drop in conductance which occurs at approximately −8° C. on the cooling curve is due to the rapid freezing of supercooled bulk water.

Figure 5:
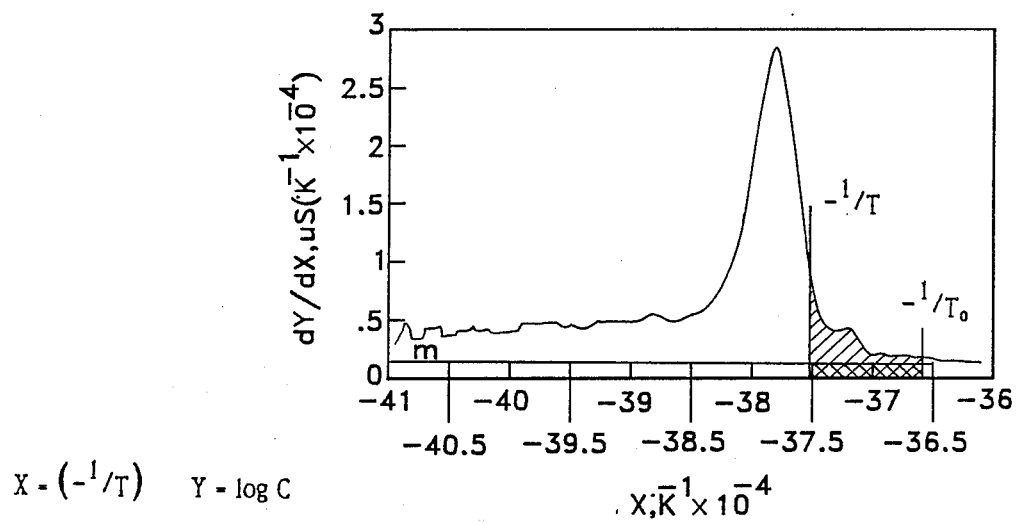
FIG. 5 is a graphic diagram of the calculation of the parameter Z in conductance phase transition porosimetry according to the invention.

FIG. 5 illustrates graphically the calculation of the parameter Z which is defined in equation 16. Plotted on this graph is the first derivative of the $\log_{10}$ of the conductance with respect to the negative inverse of the absolute temperature versus the negative inverse of the absolute temperature for the warming cycle of the test conducted on the sample (Vycor glass). The integration of these data over finite intervals, as illustrated in FIG. 4, give the parameter Z as a function of the negative inverse of the absolute temperature. Combining this relationship with the plastic ice model relationship expressed in equation 1 gives Z as a function of pore radius. The relative conducting pore volume as a function of pore radius is calculated using equation 18.

Figure 6:
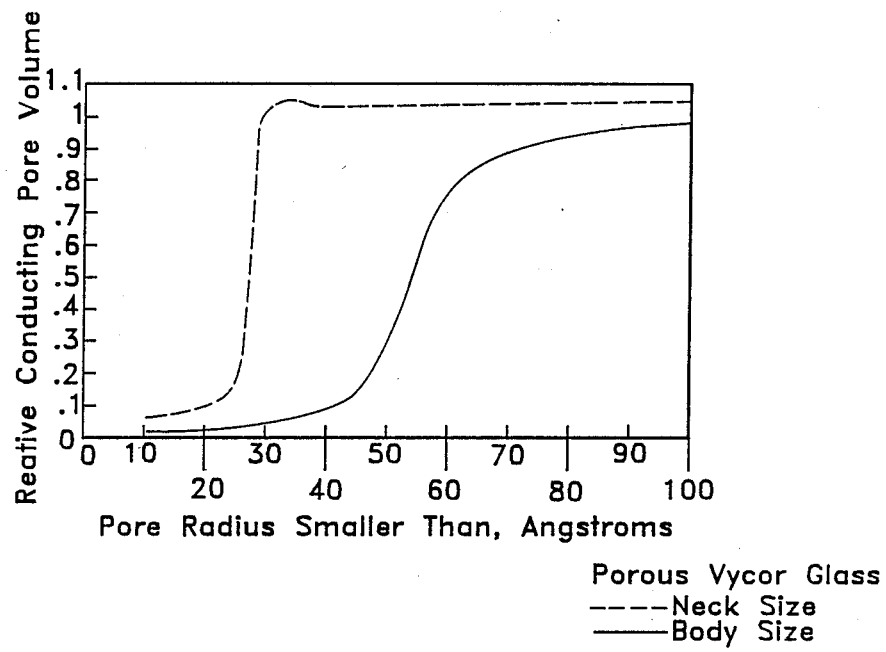
FIG. 6 is a graphic representation of conductometric pore size distribution for a pore material sample according to analysis under the invention.
Figure 7:
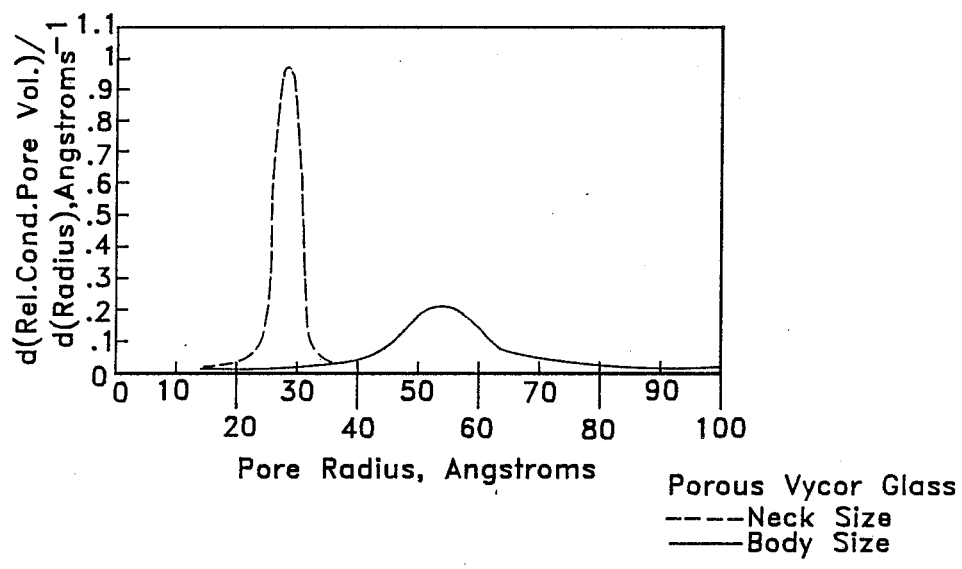
FIG. 7 is another graphic representation of conductometric pore size distribution of a sample according to the invention.

FIGS. 6 and 7 illustrate two graphical means of presenting conductometric pore size distributions.

The included preferred embodiment is given by way of example only and not by way of limitation to the invention, which is solely described by the claims herein. Variations obvious to one skilled in the art will be included within the invention defined by the claims.

For example, in the preferred embodiment, conductivity meter 28 is a Solomat model no. 2009. This meter's high frequency alternating current excitation, and the use of stainless steel or tungsten electrodes minimize polarization effects. The instrument has a resolution of 0.01 micro-siemens (μS). Digitized conductance output from the meter is relayed to digital computer 38.

Thermistor 30 is manufactured by Thermometrics and is used as a variable resistor in a square wave oscillator 40. The oscillator's output frequency varies with the corresponding changes in the resistance of the thermistor. Computer 38 then measures the period of the square wave.

Cryrostat 12 is manufactured by Haake and is filled with iso-propyl alcohol. Temperature in cyrostat 12 is controlled by the computer 38 through digital to analog converter 48.

Computer 38, an Apple IIe, is equipped with two input-output cards 44 and 46 from John Bell Engineering. These cards serve as an interface between the measurements circuitry and computer 38. Software was developed to allow computer 38 to control the temperature of the cryrostat 12, gather test data, perform necessary data processing, and output the processed data either to computer 38's video monitor or a Hewlett-Packard plotter 52.

What is claimed is:

1. A method for determination of the pore structure and porosity characteristics of porous materials using electrical conductance comprising the steps of:

saturating a porous material, comprising a sample, with an electrolytic solution;

varying the temperature of the saturated sample to cause at least a portion of the electrolytic solution in the sample to change phase;

measuring the temperature and electrical conductance of the sample as temperature of the sample is varied.

2. The method of claim 1 wherein the electrolytic solution is comprised in part of water.

3. The method of claim 1 wherein the electrolytic solution is comprised of an ionic solution.

4. The method of claim 1 wherein measurement of conductance is accomplished by positioning first and second electrodes at spaced apart positions along the sample, the electrodes being connected to an electrical conductance meter, and measuring the electrical conductance between the electrodes.

5. The method of claim 1 wherein the temperature is varied so as to change the temperature in and around the sample along a range on either side of and including the freezing point of water.

6. The method of claim 1 wherein the temperature is varied in or around the sample so that it is in a range on either side of and including the freezing point of the electrolytic solution.

7. The method of claim 1 wherein the electrical conductance of the sample is measured as a function of temperature.

8. The method of claim 1 wherein the temperature is controlled by a control unit means.

9. The method of claim 8 wherein the control unit means further receives measurements of temperature and electrical conductance and records the same.

10. The method of claim 1 wherein the pore structure and porosity characteristics include but are not limited to relative conducting pore volume, pore size, pore size distribution, and related parameters.

* * * * *